United States Patent [19]
Yim

[11] Patent Number: 5,486,356
[45] Date of Patent: Jan. 23, 1996

[54] DEODORANT COMPOSITION COMBINING TRANSITION METAL OXIDE OR ALLOY WITH CATALYTIC METAL ON CARRIER

[75] Inventor: Seung-jae Yim, Seoul, Rep. of Korea

[73] Assignee: Fuji Photo Film Co., Ltd., Kanagawa, Japan

[21] Appl. No.: 94,383

[22] Filed: Jul. 21, 1993

Related U.S. Application Data

[63] Continuation of Ser. No. 889,139, May 27, 1992, abandoned.

[30] Foreign Application Priority Data

May 30, 1991 [KR] Rep. of Korea .......... 91-8881

[51] Int. Cl.⁶ ..................................... A01N 25/12
[52] U.S. Cl. .......... 424/76.1; 424/76.3; 424/76.9; 424/405
[58] Field of Search ..................... 424/405, 401, 424/489, 408, 409, 76.1, 76.5, 76.9, 76.3

[56] References Cited

U.S. PATENT DOCUMENTS

| | | | |
|---|---|---|---|
| 1,170,056 | 2/1916 | Englemann | 424/489 |
| 1,482,906 | 7/1922 | Allen | 424/489 |
| 2,038,694 | 4/1936 | Wiggins | 167/72 |
| 2,112,167 | 3/1938 | Laszlo | 167/72 |
| 4,006,175 | 2/1977 | Termin et al. | 260/438.5 R |
| 5,015,521 | 5/1991 | Fujii et al. | 428/220 |
| 5,122,418 | 4/1992 | NaKane et al. | 424/401 |
| 5,244,667 | 9/1993 | Hagiwara et al. | 424/409 |

Primary Examiner—Thurman K. Page
Assistant Examiner—Neil Levy
Attorney, Agent, or Firm—Sughrue, Mion, Zinn, Macpeak & Seas

[57] ABSTRACT

A deodorant comprising: (1) (a) a carrier formed of 70–94 percent by weight of at least one inorganic material selected from a group consisting of silica gel, MgO, and talc; and (b) 6–30 percent by weight of transition metal oxide or alloy; and (2) a catalytic metal adsorbed on the carrier in an amount of 0.2–1 percent by weight based on weight of the carrier, and a method for the production thereof.

4 Claims, No Drawings

DEODORANT COMPOSITION COMBINING TRANSITION METAL OXIDE OR ALLOY WITH CATALYTIC METAL ON CARRIER

This is a Continuation of application Ser. No. 07/889,139 filed May 27, 1992, now abandoned.

FIELD OF THE INVENTION

The present invention relates to a deodorant effective for eliminating various offensive odors and a manufacturing method thereof, wherein the occurrence of catalytic poisons in the deodorant is remarkably decreased, thereby improving the shelf life of the deodorant.

BACKGROUND OF THE INVENTION

Various deodorizing methods have been suggested to eliminate environmental or industrial odors resulting from the work place, toilets, refrigerators, refuse bins, etc. The following methods are given as examples of these conventional deodorizing methods: (i) use of the odor-masking effect of an aroma, (ii) adsorption using a porous inorganic material, such as activated carbon, as a deodorant, (iii) odor-elimination by a chemical reaction of an adsorbent whose main component is citric acid or maleic acid, (iv) deodorizing with ozone, and (v) deodorizing with a deodorant whose raw materials are vitamin C and a ferrous sulfate.

However, such conventional deodorizing methods have the following problems. According to method (i), the odor is not essentially eliminated. In method (ii), the adsorption capability of the deodorant is limited, so that its adsorptivity decreases early. Method (iii) is available for adsorbing ammonia, amine, etc., but cannot be used for eliminating mercaptans. Since method (iv) uses an oxidizer, a secondary pollutant is produced. The deodorant according to method (v) is very susceptible and sensitive to temperature variations.

Moreover, a conventional deodorant prepared by immersing a simple inorganic carrier in a catalytic solution of a noble metal such as Ni, Pt, Ru, Rh, Ag, Co, or Ir, has a somewhat greater deodorizing effect and is useful for eliminating mercaptans. However, since sulfur molecules generated during decomposition of the mercaptan bond strongly to the noble metal, the catalytic activity of the noble metal is lowered over time. Moreover, regeneration of the deodorant by heating is difficult.

SUMMARY OF THE INVENTION

In consideration of the above-described disadvantages of the conventional deodorants and methods, the inventor of the present invention has recognized that, since oxygen has higher electronegativity than sulfur, covalent bond strength between the catalytic metal and oxygen is weaker than that between the catalytic metal and sulfur, so that the regeneration of a catalyst by heating is remarkably improved by adding a transition metal oxide or alloy thereto, and a catalyst comprising a catalytic metal and a transition metal oxide or alloy can be used as a deodorizer. On the basis of this recognition, the present invention has been accomplished.

Therefore, an object of the present invention is to provide a novel deodorant which comprises a carrier composed of a transition metal oxide or alloy, and a catalytic metal adsorbed on the carrier.

Another object of the present invention is to provide a method for manufacturing the above deodorant.

To achieve the above objects, the present invention provides a deodorant comprising:

(1) (a) a carrier formed of 70–94 percent by weight of at least one inorganic material selected from a group consisting of silica gel, MgO, and talc, and (b) 6–30 percent by weight of a transition metal oxide or alloy; and (2) 0.2–1 percent by weight (on the basis of the weight of the carrier) of a catalytic metal adsorbed on the carrier.

DETAILED DESCRIPTION OF THE INVENTION

Preferably, the carrier is a porous carrier which comprises 20–50 percent by weight of silica gel, 20–40 percent by weight of MgO, 20–40 percent by weight of talc, and 6–30 percent by weight of the transition metal oxide or alloy.

Examples of transition metals suitable for use in the transition metal oxide or alloy of the present invention include Cr, Ce, Mn, Mo, Re, Ti, V, W, Zn, Zr, etc. The oxides or alloys of these transition metals may be used alone or as mixtures of two or more thereof. More particularly, examples of transition metal oxides and alloys suitable for use in the present invention include $CrO_2$, $CeO_2$, $MnO_2$, $MoO_2$, $Re_2O_7$, $TiO_2$, $V_2O_5$, $WO_3$, $ZnO$, $ZrO_2$, etc.

Examples of a catalytic metal suitable for use in the present invention include noble metals such as Pt, Ru, Rh, Pd, Ag, Ir, etc., and non-noble metals such as Fe, Co, Ni, etc. These catalytic metals may be used alone or as mixtures of two or more thereof.

To achieve another object of the present invention, a method is provided for manufacturing a deodorant comprising the steps of immersing a carrier formed of 70–94 percent by weight of at least one inorganic material selected from a group consisting of silica gel, MgO, and talc, and 6–30 percent by weight of a transition metal oxide or alloy, in an aqueous catalytic metal complex compound solution, and then drying, calcining, and reducing the carrier. In this method, the carrier is immersed for about 30–60 second in an aqueous solution containing 0.1–2 moles per liter of a dissolved catalytic metal complex compound. Examples of catalytic metal complex compounds for use in the present invention include $Pt(NH_3)_4Cl_2$, $H_2PtCl_6 \cdot xH_2O$, $H_2IrCl_6 \cdot xH_2O$, $Fe(NO_3)_3 \cdot 9H_2O$, $RhCl_3$, $Ni(NO_3)_2 \cdot 6H_2O$, etc.

The aqueous catalytic metal complex compound solution can be saturated or dilute as long as the carrier immersion time and catalytic metal complex compound concentration are managed to preferably provide an amount of catalytic metal adsorbed on the carrier which is 0.2–1 percent by weight based on weight of the carrier.

A method for preparing a deodorant according to the present invention is now described in greater detail. First, inorganic carrier components are prepared and mixed according to a predetermined composition ratio. In this regard, the composition ratio of the components is such that an inorganic material selected from the group consisting of silica gel, MgO, and talc is 70–94 percent by weight, and a transition metal oxide or alloy is 6–30 percent by weight.

Then, this mixture is put into a 2–6 percent by weight of aqueous polyvinyl alcohol solution having a mass of 3–6 times that of the inorganic carrier, which is uniformly mixed in a ball mill for 1–5 hours, thereby obtaining a slurry. This slurry is dried in a convection drier at 80°–120° C. for 3–5 hours, and then molded under a pressure of 100–500 kg/cm², which is then sintered at 600°–800° C. for 0.5–3 hours, so that a porous carrier is prepared whose specific surface area (BET) is more than 150 m²/g and whose density is below 1 g/cm³.

This carrier thus prepared is immersed into an aqueous solution containing 0.1–2 moles per liter of a catalytic metal complex compound for 30–60 seconds. Then the carrier is dried in a convection drier at a temperature of 100°–200° C. for 1–5 hours, is calcined in a tubular furnace at 100°–500° C. for 1–5 hours, and then is reduced in the tubular furnace at 100°–500° C. under a hydrogen flow of 1–5 cc per second for one gram of carrier, thereby completing manufacture of the deodorant.

The deodorant of the present invention thus obtained easily adsorbs offensive-smelling materials such as ammonia, amine, methyl-mercaptan, carbon disulfide, and the like.

Also, when the offensive-smelling materials are saturately adsorbed in the deodorant of the present invention while being used, thermolysis of the adsorbed offensive-smelling materials can be easily carried out by heating the deodorant to 100°–200° C. in a separate heater or the heater provided for defrosting a refrigerator, and by the catalytic action of the catalytic metals.

During thermolysis, an oxide or an alloy of a transition metal such as Cr, Mn, Mo, etc., used in the present invention, provides an adsorption site for decomposition-generated sulfur atoms before undesired adsorption of sulfur atoms to the catalytic metal. Thus, the so-called "sulfur poisoning" phenomenon caused by the adsorption of sulfur by a catalytic metal is remarkably decreased in the deodorant of the present invention. Therefore, since the activity of the catalytic metal catalyst in the deodorant is maintained, the efficiency of the deodorant is improved, and its shelf life is also extended.

That is, the reduction in activity of the catalytic metal catalyst due to catalytic poisoning is substantially curtailed in the deodorant of the present invention as compared with the conventional deodorant. Thus, the catalytic efficiency of the catalytic metal is excellent, and the shelf life of the catalytic metal catalyst is also enhanced.

By simply heating the deodorant of the present invention to 100°–200° C. in a separate heater, adsorbed offensive-smelling materials are easily decomposed, so that the regeneration of the catalytic metal catalyst is simplified. Accordingly, if such a deodorant is used in a refrigerator, the deodorant of the present invention is advantageous in that the catalyst can be easily regenerated, using the existing heater provided for defrosting without the need to install an additional heater.

Hereinafter, the present invention will be described in detail with reference to a preferred embodiment, which, however, shall not be interpreted in a limiting sense.

EXAMPLE

An inorganic mixture is mixed with 3 percent by weight of a polyvinyl alcohol solution with a mass five times the inorganic mixture in a ball mill for two hours, where the inorganic mixture has the following composition:

silica gel 35 percent by weight

MgO 25 percent by weight talc 25 percent by weight $CeO_2$ 10 percent by weight $CrO_2$ 5 percent by weight Thereafter, the obtained slurry is dried in a convection drier at 100° C. for four hours, is molded under a pressure of 250 kg/cm², and then is sintered at 700° C. for two hours. The carrier thus obtained is immersed for 45 seconds in an aqueous solution containing one mole per liter of $Pt(NH_3)_4Cl_2$, and the carrier is dried in a convection drier at 150° C. for three hours. The dried material is calcined in a tubular furnace at 300° C. for three hours, and the calcined product is reduced in a tubular furnace at 300° C. under a hydrogen flow of 3 cc per second for one gram of the carrier, thus obtaining the deodorant.

Applying 100 ppm mercaptan as an offensive-smelling material at 200° C., and using air flow rates of 8 and 4 cc per second for one gram of the carrier, the decomposition rate of methyl-mercaptan according to various periods of time was measured by gas chromatography. The results of the measurement is shown in Table 1 below.

COMPARATIVE EXAMPLE

The same conditions and measurement method as in the above example were used in this comparison example except that the transition metal oxide was not present in the carrier. These results are also represented in Table 1.

TABLE 1

| | decomposition rate of Methyl-mercaptan with Time-Passage (%) | | | | |
|---|---|---|---|---|---|
| | 1 hr. | 2 hrs. | 3 hrs. | 4 hrs. | 5 hrs. |
| Example | 40 | 58 | 68 | 74 | 80 |
| Comparative example | 33 | 49 | 53 | 55 | 56 |

While the invention has been described in detail and with reference to specific embodiments thereof, it will be apparent to one skilled in the art that various changes and modifications can be made therein without departing from the spirit and scope thereof.

What is claimed is:

1. A deodorant consisting essentially of:
   (1) a carrier formed of (a) 70–94 percent by weight of silica gel, MgO, and talc; and (b) 6–30 percent by weight of transition metal oxide or alloy; and
   (2) a catalytic metal adsorbed on said carrier in an amount of 0.2–1 percent by weight based on weight of said carrier,
   wherein said carrier comprises a porous carrier containing 20–50 percent by weight of silica gel, 20–40 percent by weight of MgO, 20–40 percent by weight of talc, and 6–30 percent by weight of transition metal oxide or alloy, and
   wherein said catalytic metal has a covalent bond strength with oxygen which is weaker than its covalent bond strength with sulfur.

2. A deodorant as claimed in claim 1, wherein said transition metal oxide or alloy comprises at least one metal cation selected from the group consisting of Cr, Ce, Mn, Mo, Re, Ti, V, W, Zn, and Zr.

3. A deodorant as claimed in claim 1, wherein said catalytic metal comprises at least one catalytic metal selected from the group consisting of Pt, Ni, Ru, Rh, Pd, Ag, Fe, Co, and Ir.

4. A deodorant as claimed in claim 1, wherein said transition metal oxide or alloy comprises a combination of different types of transition metal oxides or alloys.

\* \* \* \* \*

UNITED STATES PATENT AND TRADEMARK OFFICE
CERTIFICATE OF CORRECTION

PATENT NO. : 5,486,356
DATED      : January 23, 1996
INVENTOR(S) : Seung-jae Yim It is certified that error appears in the above-indentified patent and that said Letters Patent is hereby corrected as shown below:

On the cover page, in item [73] Assignee:, delete "Fuji Photo Film Co., Ltd., Kanagawa, Japan" and insert therefor --Samsung Electronics Co., Ltd., Suwon, Republic of Korea--.

Signed and Sealed this

Thirteenth Day of May, 1997

Attest:

BRUCE LEHMAN

*Attesting Officer*  *Commissioner of Patents and Trademarks*